US009272152B2

(12) United States Patent
LaLonde et al.

(10) Patent No.: US 9,272,152 B2
(45) Date of Patent: Mar. 1, 2016

(54) REMOTE PROGRAMMING OF MRI SETTINGS OF AN IMPLANTABLE MEDICAL DEVICE

(75) Inventors: John LaLonde, Lake Elmo, MN (US); James Kalgren, Lino Lakes, MN (US); Kenneth P. Hoyme, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 21 days.

(21) Appl. No.: 13/591,469

(22) Filed: Aug. 22, 2012

(65) Prior Publication Data

US 2013/0053920 A1    Feb. 28, 2013

Related U.S. Application Data

(60) Provisional application No. 61/529,592, filed on Aug. 31, 2011.

(51) Int. Cl.
*A61N 1/08* (2006.01)
*A61N 1/37* (2006.01)
*A61N 1/372* (2006.01)

(52) U.S. Cl.
CPC ............... *A61N 1/3718* (2013.01); *A61N 1/08* (2013.01); *A61N 1/37235* (2013.01)

(58) Field of Classification Search
CPC .... A61N 1/3718; A61N 1/08; A61N 1/37235
USPC .............................................. 607/31, 59–63
See application file for complete search history.

(56) References Cited

U.S. PATENT DOCUMENTS

| 5,724,985 | A | 3/1998 | Snell et al. |
|---|---|---|---|
| 5,832,488 | A | 11/1998 | Eberhardt |
| 6,356,789 | B1 | 3/2002 | Hinssen et al. |
| 6,497,655 | B1 | 12/2002 | Linberg et al. |
| 6,725,200 | B1 | 4/2004 | Rost |
| 6,804,558 | B2 | 10/2004 | Haller et al. |

(Continued)

FOREIGN PATENT DOCUMENTS

| WO | WO-2011047493 | 4/2011 |
|---|---|---|
| WO | WO-2013032864 | 3/2013 |

OTHER PUBLICATIONS

"Heart Patients Test World's First 'Anytime' Health Assessment Booth", http://www.medicalnewstoday.com/printerfriendlynews.php?newsid=223430, accessed Mar. 22, 2013 (3 pages) Apr. 27, 2011.

(Continued)

*Primary Examiner* — Rex R Holmes
(74) *Attorney, Agent, or Firm* — Pauly, DeVries Smith & Deffner, LLC (57) ABSTRACT

A system and method are described herein including an implantable medical device (IMD) configured to be programmed with magnetic resonance imaging (MRI) settings for use during an MRI scan, wherein the IMD stores identity data that uniquely identifies the IMD or a patient having the IMD. The system includes an external storage media configured to receive MRI settings associated with the IMD and configured to store the MRI settings associated with the IMD. The system also includes a programmer configured to retrieve identity data from IMD, retrieve MRI settings associated with the IMD from the external storage media and program the IMD using the MRI settings.

19 Claims, 8 Drawing Sheets

(56) References Cited

U.S. PATENT DOCUMENTS

| | | | |
|---|---|---|---|
| 6,880,085 B1 | 4/2005 | Balczewski et al. |
| 7,039,810 B1 | 5/2006 | Nichols |
| 7,060,031 B2 | 6/2006 | Webb et al. |
| 7,092,761 B1 | 8/2006 | Cappa et al. |
| 7,181,505 B2 | 2/2007 | Haller et al. |
| 7,418,296 B2 | 8/2008 | Freeberg |
| 7,561,915 B1 | 7/2009 | Cooke et al. |
| 7,565,197 B2 | 7/2009 | Haubrich et al. |
| 7,761,167 B2 | 7/2010 | Bennett et al. |
| 7,840,276 B2 | 11/2010 | Weispfenning et al. |
| 7,853,318 B2 | 12/2010 | Wedan |
| 7,873,412 B2 | 1/2011 | Wedan |
| 8,090,443 B2 | 1/2012 | Min et al. |
| 8,295,938 B2 | 10/2012 | Goetz et al. |
| 8,299,899 B2 | 10/2012 | Frysz et al. |
| 8,347,365 B2 | 1/2013 | Jelatis et al. |
| 2003/0028883 A1 | 2/2003 | Billmaier et al. |
| 2005/0070786 A1 | 3/2005 | Zeijlemaker et al. |
| 2006/0025820 A1 | 2/2006 | Phillips et al. |
| 2006/0173718 A1 | 8/2006 | Murphy |
| 2007/0136098 A1 | 6/2007 | Smythe et al. |
| 2007/0185547 A1 | 8/2007 | Hoyme et al. |
| 2007/0265685 A1 | 11/2007 | Zeijlemaker |
| 2008/0082144 A1 | 4/2008 | Marcotte et al. |
| 2008/0221638 A1 | 9/2008 | Wedan et al. |
| 2008/0275529 A1 | 11/2008 | North et al. |
| 2009/0048644 A1 | 2/2009 | Stahmann et al. |
| 2009/0058635 A1 | 3/2009 | LaLonde et al. |
| 2009/0058636 A1 | 3/2009 | Gaskill et al. |
| 2009/0062887 A1 | 3/2009 | Mass et al. |
| 2009/0063187 A1 | 3/2009 | Johnson et al. |
| 2009/0063193 A1 | 3/2009 | Barton et al. |
| 2009/0138058 A1* | 5/2009 | Cooke et al. | 607/5 |
| 2009/0157127 A1 | 6/2009 | Sowder et al. |
| 2010/0069991 A1 | 3/2010 | Hoyme et al. |
| 2010/0087892 A1 | 4/2010 | Stubbs et al. |
| 2010/0106215 A1 | 4/2010 | Stubbs et al. |
| 2010/0137945 A1 | 6/2010 | Gadagkar et al. |
| 2010/0137946 A1 | 6/2010 | Gadagkar et al. |
| 2010/0137947 A1* | 6/2010 | Gadagkar et al. | 607/60 |
| 2010/0152806 A1 | 6/2010 | Levine et al. |
| 2010/0211123 A1 | 8/2010 | Stubbs et al. |
| 2011/0077706 A1* | 3/2011 | Ellingson et al. | 607/17 |
| 2011/0196449 A1* | 8/2011 | Jenison | 607/60 |
| 2011/0196450 A1* | 8/2011 | McClure et al. | 607/60 |

OTHER PUBLICATIONS

"Florida hospital tests programming heart devices via iPad", http://www.healthcareitnews.com/news/florida-hospital-tests-programming-heart-devices . . . , accessed Dec. 12, 2011 (2 pages).

"International Search Report and Written Opinion from International", PCT Application No. US/2012/052099, mailed Nov. 29, 2012, pp. 1-13.

"Communication Pursuant to Rules 161(1) and 162 EPC", for EP Application No. 12759302.8, mailed May 14, 2014 (2 pages).

"International Preliminary Report on Patentability", for PCT/US2012/052099, mailed Mar. 13, 2014 (8 pages).

"Response to Communication Pursuant to Rules 161(1) and 162 EPC", for European Patent Application No. 12759302.8, mailed May 14, 2014 and filed with the EPO Nov. 12, 2014 (15 pages).

* cited by examiner

REMOTE PROGRAMMING OF MRI SETTINGS OF AN IMPLANTABLE MEDICAL DEVICE

This application claims the benefit of U.S. Provisional Application No. 61/529,592, filed Aug. 31, 2011, the contents of which are herein incorporated by reference.

FIELD OF THE INVENTION

The invention relates to implantable medical devices, such as cardiac rhythm management devices, and more particularly, to methods and systems for programming such devices in advance of a magnetic resonance imaging (MRI) procedure.

BACKGROUND OF THE INVENTION

Many different types of medical devices are implanted within patients to provide medical therapy. One type of an implanted medical device is a cardiac rhythm management device, such as a pacemaker or implantable defibrillator. Cardiac rhythm management (CRM) devices are used to provide medical therapy to patients who have a disorder related to cardiac rhythm, such as bradycardia or tachycardia.

Magnetic resonance imaging (MRI) is a method of visualizing body tissues of a patient, primarily to identify pathological conditions or to visualize physiological structure for purposes of medical diagnosis and therapy. MRI relies on subjecting the body tissue of interest to a very strong uniform magnetic field, up to about 30,000 gauss, as well as a moderate strength but variable magnetic field of around 200 gauss. In the presence of these uniform and gradient magnetic fields, a radio frequency (RF) pulse is transmitted from a coil to the body tissue. Hydrogen atoms within the body tissue have a magnetic moment and tend to line up with the direction of the applied magnetic fields. Some of these hydrogen atoms will align facing one direction and others will align facing an opposite direction, such that most of the hydrogen atoms facing in alternating directions will tend to cancel each other out. However, a small percentage (but a significant absolute number) of hydrogen atoms will be unbalanced, or not cancelled out. The applied RF pulse tends to cause the unbalanced hydrogen protons to spin, or resonate, in a particular direction and at a particular frequency. When this RF pulse is turned off, the spinning hydrogen protons revert to their earlier, aligned position, and release their excess energy. The RF coil of the MRI machine is capable of detecting this emitted energy and transmitting a corresponding signal to a processor that transforms the signal to an image of the body tissue. Because different tissues have different characteristic responses to the application of the RF pulse in the presence of the magnetic fields, these differences can be utilized to prepare an image showing areas of contrasting tissue types.

MRI techniques have proven to be very effective at diagnosing certain medical conditions and allowing for patients to receive timely, appropriate medical therapy. However, in many cases patients having an implanted medical device are contraindicated for MRI and MRI may be inappropriate for those patients.

During imaging, the electromagnetic radiation produced by the MRI system may interfere with the operation of an IMD. In the case of cardiac devices, the presence of strong magnetic fields and RF energy during an MRI scan may prevent the charging of a high voltage capacitor within the cardiac device, which can affect the ability of the cardiac device to deliver electrical shocks to the patient when an event such as a tachyarrhythmia occurs. The RF energy and/or time varying gradient fields may prevent the sensing and detection of tachyarrhythmias by cardiac devices. The MRI system may also affect other types of implantable medical devices (IMDs).

Some embodiments of IMDs provide for a method of operating an IMD in the presence of an MRI environment using particular MRI settings for the IMD. Examples of patents and patent publications that describe such methods and options for MRI settings for an IMD include U.S. Published Patent Application No. 2010-0087892A1, Stubbs et al.; U.S. Published Patent Application No. 2010-0106215A1, Stubbs et al.; U.S. Published Patent Application No. 2010-0211123A1, Stubbs et al.; U.S. Published Patent Application No. 2008-0221638A1, Wedan et al.; U.S. Pat. No. 7,853,318, Wedan and U.S. Pat. No. 7,873,412, Wedan; which are each incorporated by referenced herein in its entirety.

SUMMARY

A system is described herein including an implantable medical device (IMD) configured to be programmed with magnetic resonance imaging (MRI) settings for use during an MRI scan, wherein the IMD stores identity data that uniquely identifies the IMD or a patient having the IMD. The system further includes an external storage media configured to receive MRI settings associated with the IMD and configured to store the MRI settings associated with the IMD. The system also includes a programmer configured to retrieve identity data from IMD, retrieve MRI settings associated with the IMD from the external storage media and program the IMD using the MRI settings.

In another embodiment, the system includes an implantable medical device (IMD) configured to be programmed with magnetic resonance imaging (MRI) settings for use during an MRI scan and the IMD storing identity data that uniquely identifies the IMD or a patient having the IMD. The system also includes a server configured to receive MRI settings associated with the IMD and configured to store the MRI settings associated with the IMD and a portable programmer. The portable programmer includes a housing configured for portability by a user, a first communication module in the housing configured to communicate with the server to retrieve the MRI settings that are associated with the IMD, a device communication module connectible to and disconnectible from the housing and configured to inductively communicate with the IMD to retrieve the identity data and program the IMD with the MRI settings, and a power source in the housing configured to supply power for components of the programmer.

A method is described herein for conducting a magnetic resonance imaging (MRI) scan of a patient having an implantable medical device (IMD) including the steps of storing MRI settings for an IMD on an external storage media, wherein the IMD stores identity data that uniquely identifies the IMD or the patient and identifying the IMD or patient using a programmer to communicate with the IMD. The method further includes the step of using the programmer to retrieve the MRI settings from the external storage media.

The invention may be more completely understood by considering the detailed description of various embodiments of the invention that follows in connection with the accompanying drawings.

While the invention may be modified in many ways, specifics have been shown by way of example in the drawings and will be described in detail. It should be understood, however, that the intention is not to limit the invention to the particular embodiments described. On the contrary, the intention is to cover all modifications, equivalents, and alternatives following within the scope and spirit of the invention as defined by the claims.

DETAILED DESCRIPTION OF THE INVENTION

The invention relates to implantable medical devices such as cardiac rhythm management devices, and more particularly, to methods and systems for efficiently programming such devices. Still more particularly, embodiments of the invention relate to efficiently programming cardiac rhythm management devices in advance of a magnetic resonance imaging (MRI) procedure.

Only certain medical professionals have received training in making programming changes to IMDs. That training involves familiarity with the particular model of IMD and its purpose, functions and setting options, knowledge of the relevant patient information that needs to be gathered and checked before programming, and familiarity with programming hardware used to accomplish the programming. These highly-trained individuals are in great demand, and are not present in every medical facility. If IMD settings need to be modified quickly or before a procedure, it can be challenging to locate such a highly-training professional to be present at the specific location along with the necessary programming hardware.

One example of a procedure that often requires changes to the settings of an IMD is magnetic resonance imaging (MRI). To address this concern, many IMDs are capable of MRI settings that reduce the risks associated with an MRI. Another concern is that patients with IMDs need to be evaluated by a knowledgeable health care professional before permitting an MRI procedure.

In one embodiment, a health care professional who is trained in IMD programming and in evaluating patients provides MRI settings for a particular IMD after evaluating the patient having the IMD. The MRI settings are provided to an external storage media where the MRI settings are stored. The MRI settings are stored on the external storage media in advance of the scheduled time for the MRI procedure.

The external storage media can be a network server that is connected to the programmer used by the health care professional by the Internet or by another network. The external storage media can also be a portable storage device, such as a magnetic card or jump drive.

Other information can be provided along with the MRI settings and can include identity data uniquely identifying the IMD or the patient. This group of information including the MRI settings can be referred to as an MRI prescription. The MRI prescription can also include computer readable instructions to carry out the programming of the MRI settings on the IMD. In some embodiments, the MRI prescription also includes identity data to identify the health care professional who evaluated the patient and provided the MRI settings. In one embodiment, the MRI prescription also includes a timer value indicating a length of time during which the MRI settings will be active. After the expiration of the timer value, the IMD will go out of the MRI mode and the parameter settings will revert back to the pre-MRI settings, in one embodiment. The MRI prescription also includes, in some embodiments, one or more of an indication of which chambers are paced, an MRI pacing mode, an MRI pace amplitude, an MRI pace rate, and an MRI pulse width. However, the concepts described herein are not limited to these particular settings or to cardiac devices. In other embodiments, different parameter values are provided for a cardiac device. In other embodiments, parameter values are provided for other IMDs.

At the time of creating the MRI prescription, the health care professional also enters a timeframe over which the MRI prescription will be valid, in one embodiment. After the timeframe has passed, the MRI prescription cannot be retrieved from the storage media. The patient will be reevaluated and a new MRI prescription will be created.

When the patient having the particular IMD arrives at the MRI clinic, an MRI technician uses a programmer device to access identity data on the IMD which uniquely identifies the particular IMD or particular patient. The MRI technician further uses the programmer to communicate with the external storage media to retrieve the previously-stored MRI prescription, including MRI settings, and program the IMD using the MRI settings. The existence of a previously-stored valid MRI prescription indicates that the patient has been evaluated and cleared for an MRI procedure.

The programmer used by the MRI technician is able to communicate with the external storage media to retrieve the MRI settings that are associated with the IMD. A first communication module within the programmer carries out the communication with the external storage media. The programmer is also able to communicate with the IMD to determine the identity of the IMD or the patient and program the IMD with the MRI settings. The communication with the IMD is carried out by a device communication module of the programmer. The device communication module may communicate inductively, by radio frequency or other methods. The first communication module can communicate with the external storage media over a pervasive wireless network, over a wired network, or by other means. The programmer further includes a power source configured to supply power for components of the programmer. In one embodiment of such a system, the programmer has a portable housing configuration and the power supply is included in the housing.

Device Clinic Systems and Methods

Figure 1:
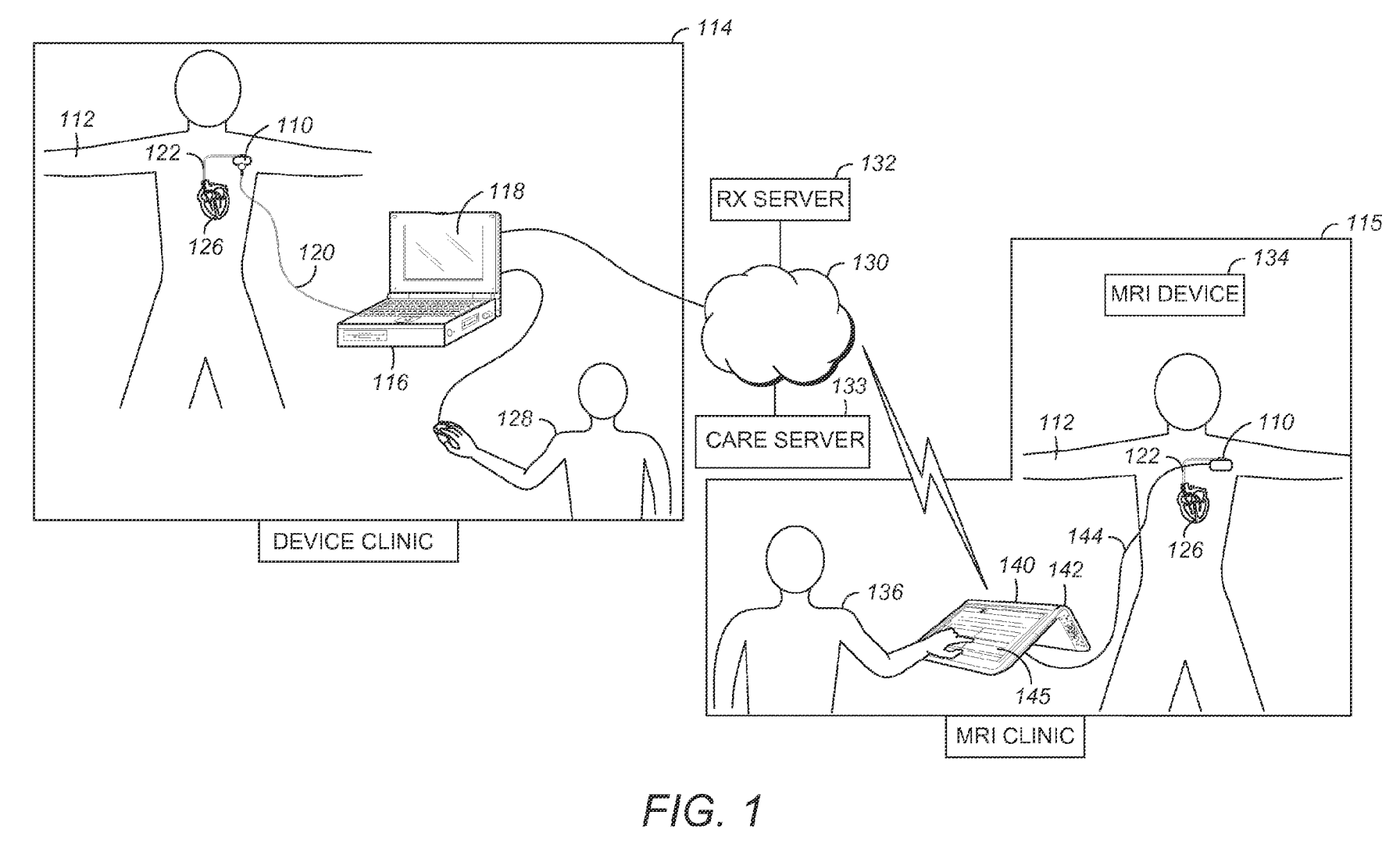
FIG. 1 is a schematic view of one embodiment of a system for remote programming of an IMD with MRI settings.

FIG. 1 is a schematic view of one embodiment of a system for remote programming of an IMD with MRI settings. In this system, an IMD 110 is shown implanted in a patient 112. The patient 112 is shown present in a device clinic 114 and, at a later time, will also be present in an MRI clinic 115. Examples of IMDs 110 include, without limitation, a cardiac device, a pacemaker, a defibrillator, a cardiac resynchronization therapy (CRT) device, an insulin pump, a loop recorder, a neurostimulator, a physiological sensor, a glucose meter or a combination of such devices. The system also includes an device clinic programmer 116 or other external device that communicates wireless signals with the IMD 110, such as by using radio frequency (RF) or other telemetry signals. Alternatively, the device clinic programmer 116 communicates inductively using a wand 120. The device clinic programmer 116 can also communicate with an external storage media. The communication with the external storage media allows storage of MRI settings that are entered using the device clinic programmer 116. In the embodiment of FIG. 1, the external storage media is a part of a server 132. It is also possible for the external storage media to be a portable storage device, such as a flash drive or magnetic card. Although the terms "server" and "prescription server" will be used to describe the storage location of the MRI settings in a number of embodiments described herein, including the embodiments of FIG. 1, it will be understood that it is also possible for the MRI settings to be stored on an external storage media different than a server.

There are many options for the hardware of the device clinic programmer 116 and some of these options will be further described herein. In addition to the wand 120, the device clinic programmer 116 includes a graphical display 118 and user input devices such as in some embodiments a keyboard and a mouse. In the device clinic setting, a health care professional 128 can use the device clinic programmer to program IMDs, record data from IMDs, allow monitoring of the implanted device and upload information to a server 132. The health care professional 128 can evaluate the patient 112, the type of IMD 110 and other factors and can determine the patient eligibility for an MRI procedure.

Although one configuration for a device clinic programmer is shown in FIG. 1, many other configurations are possible. For example, the device clinic programmer may have the shape of a laptop computer, a desktop computer, a tablet computer, a smart phone or another configuration. In FIG. 1, the device clinic programmer 116 is depicted in a ruggedized laptop computer configuration. The device clinic programmer 116 can also be referred to as a user interface or an external interface device. The device clinic programmer 116 is in communication with a server, which can be referred to as a prescription server 132. The communication link between the programmer 116 and the server 132 may be via phone lines, a wired network, the Internet 130, or any other data connection, such as a pervasive wireless network. The device clinic programmer 116 can also be used when it is not in communication with an IMD device, but is only in communication with the server 132. The device clinic programmer 116 can also be used when it is not in communication with the server 132, but is only in communication with an IMD.

Figure 2:
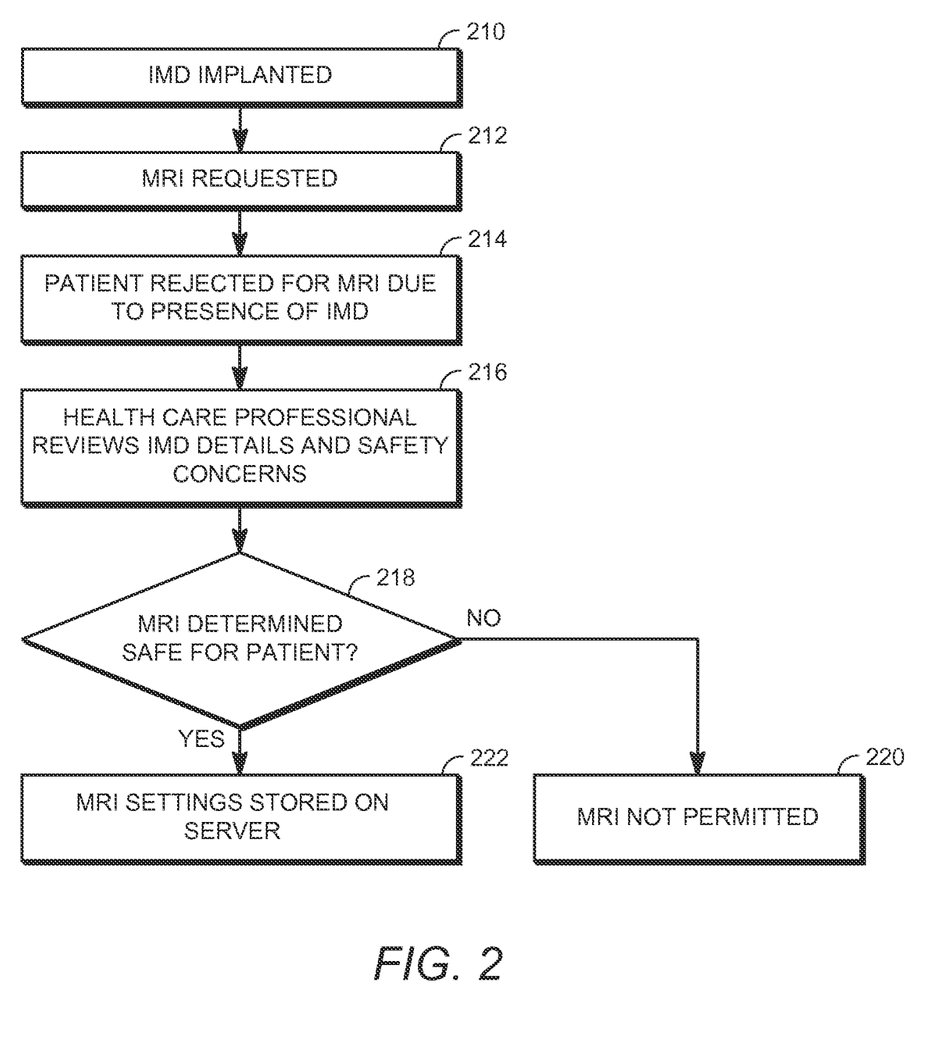
FIG. 2 is a flowchart showing a method for permitting or not permitting an MRI procedure for a patient having an IMD and for storing MRI settings.

FIG. 2 sets forth one embodiment of steps for how a patient with an IMD may be evaluated for a possible MRI procedure. In step 210, the patient undergoes an IMD implantation procedure. Later, possibly years later, the patient is identified as a candidate for an MRI procedure in step 212. In the process of preparing for the MRI, the patient may be rejected for the MRI due to the presence of the IMD in step 214. This step causes the patient to be directed to a health care professional having training related to the IMD for review of IMD details, patient condition and safety concerns related to the MRI procedure at step 216. Now referring to FIG. 1, this review by a health care professional 128 can take place in a device clinic 114 using the device clinic programmer 116 and a connection to the prescription server 132.

Again referring to FIG. 2, the health care professional determines whether an MRI procedure would be safe for the patient at step 218. If no, the MRI is not permitted at step 220. If yes, the health care professional generates an MRI prescription including MRI settings and causes those to be stored on the server 132. At this point in time in the process, the MRI settings have not yet been programmed into the IMD. Instead, the MRI settings have been stored on the server 132 for later retrieval at the time of the MRI procedure.

Particular steps that are taken by the device clinic programmer in some embodiments include interrogating the IMD to determine its status and download diagnostic and therapeutic information and displaying to the health care professional an MRI checklist. The MRI checklist is formulated to assist the professional with the assessment of whether or not an MRI should be permitted for the patient. If the health care professional determines that an MRI should be permitted, the device clinic programmer presents an MRI prescription form to the professional.

Figure 10:
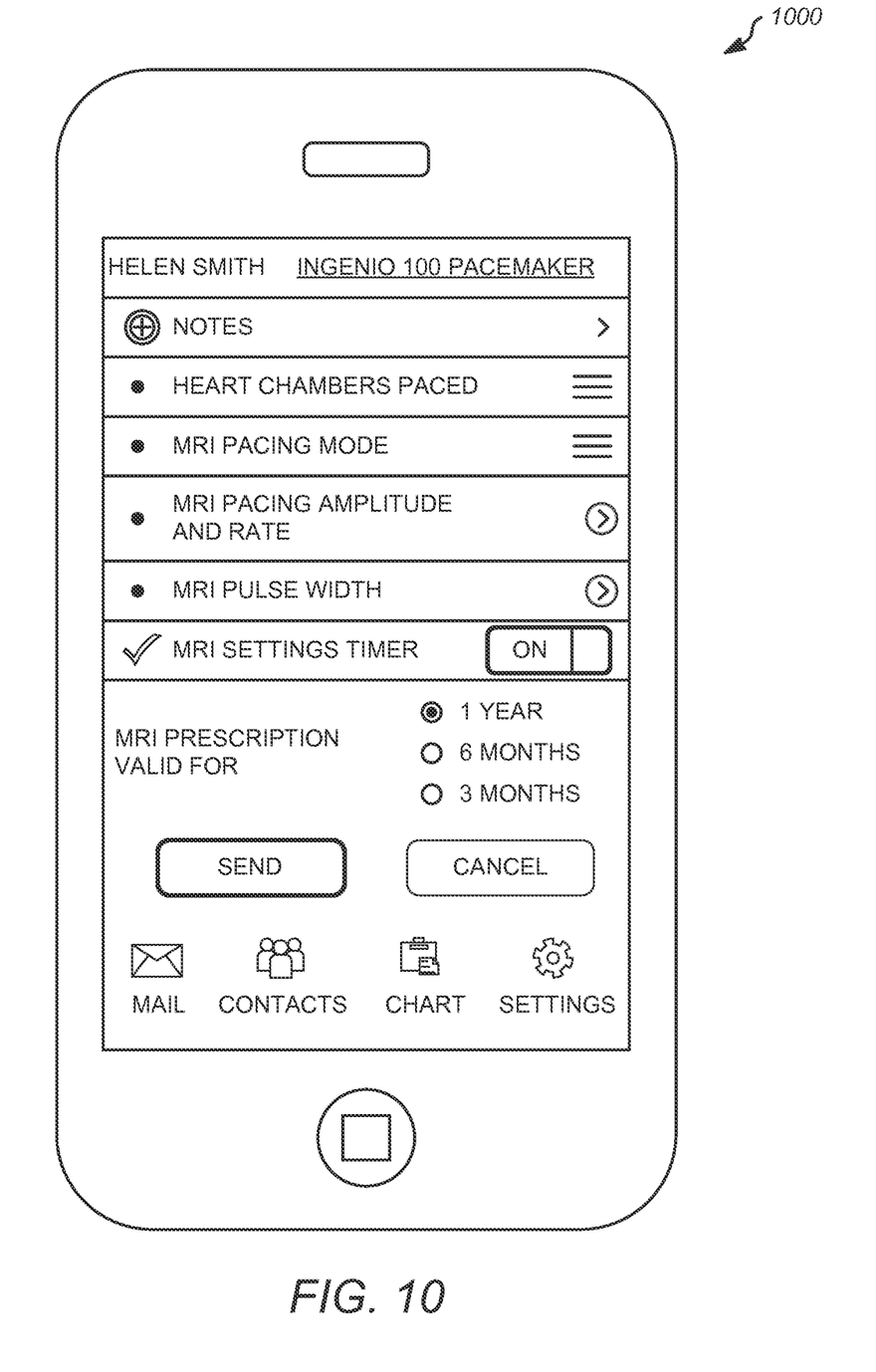
FIG. 10 is one embodiment of an MRI prescription form.

One example of an MRI prescription form 1000 is shown in FIG. 10. The MRI prescription form 1000 shown in FIG. 10 is formatted for display on a smart phone-type display. The professional uses the MRI prescription form to enter parameter data for the MRI settings. Some of the data entered are numerical values for particular parameter settings, such as the MRI timer and MRI pulse width. The MRI prescription form also includes, in some embodiments, one or more of an indication of which chambers are paced, an MRI pacing mode, an MRI pace amplitude, an MRI pace rate, an MRI settings timer and a selection for a validity timeframe. Some of the selections can be made on the portion of the form shown in FIG. 10, while some selections are made by navigating to a different screen or portion of the form for further data entry. After entry of the data into the MRI prescription form, the programmer performs a range checking step in some embodiments. The range checking step compares the entered values against expectations regarding these values, to determine if the values are correct for the particular situation. In one example, the programmer checks to see that the timer value is a positive number and that it falls in a range of 1 to 24 hours. Other numerical values for the MRI settings are also compared to an expected range in some embodiments. Examples of selections for the MRI settings timer include on, one year, six months, three months, 24 hours and one hour.

After the checking step is performed, then the device clinic programmer compiles the completed MRI prescription form into a structured text-based software program that can be executed at the MRI clinic to change the IMD settings.

On the server 132, the MRI prescription information is stored until retrieved. The MRI prescription is uniquely tagged with identity data, such as an identification number, that uniquely identifies the patient, the particular IMD or both. In one embodiment, the unique identity data stored on the IMD is a device serial number.

In some embodiments, a second server 133 or additional servers are in communication with the device clinic programmer 116 and with the MRI clinic programmer 140. The second server 133 can be a care server that allows clinicians to log in and view the details of what is happening with their patient's IMD performance or history. One example of such a system is the LATITUDE® Patient Management System that is designed for use with certain compatible pulse generators manufactured by Boston Scientific Corporation. It is also possible for the system to be connected to other servers, such as servers that store electronic medical records (EMRs) of patients. It is also possible for the programmer to communicate with a single server for multiple purposes, such as for retrieving prescriptions and for patient care, for patient care and EMRs, or for EMRs and retrieving prescriptions.

MRI Clinic Systems and Methods

Again referring to FIG. 1, the patient 112 having the IMD 110 is also depicted in an MRI clinic 115. The patient 112 would be at the MRI clinic only after the health care professional had stored the MRI settings on the server 132. At the MRI clinic 115, an MRI device 134 is available for use and an MRI professional 136 is available to do one or more of assist the patient, retrieve identity data from the IMD 110, collect demographic data from the patient, check for an MRI prescription, program MRI settings, conduct the MRI procedure, program the IMD with post-MRI settings, and send an MRI report and device report to the patient's electronic medical record and other health care professionals. The MRI professional 128 uses an MRI clinic programmer 140 to communicate with the IMD 110 and to communicate with the server 132.

Figure 3:
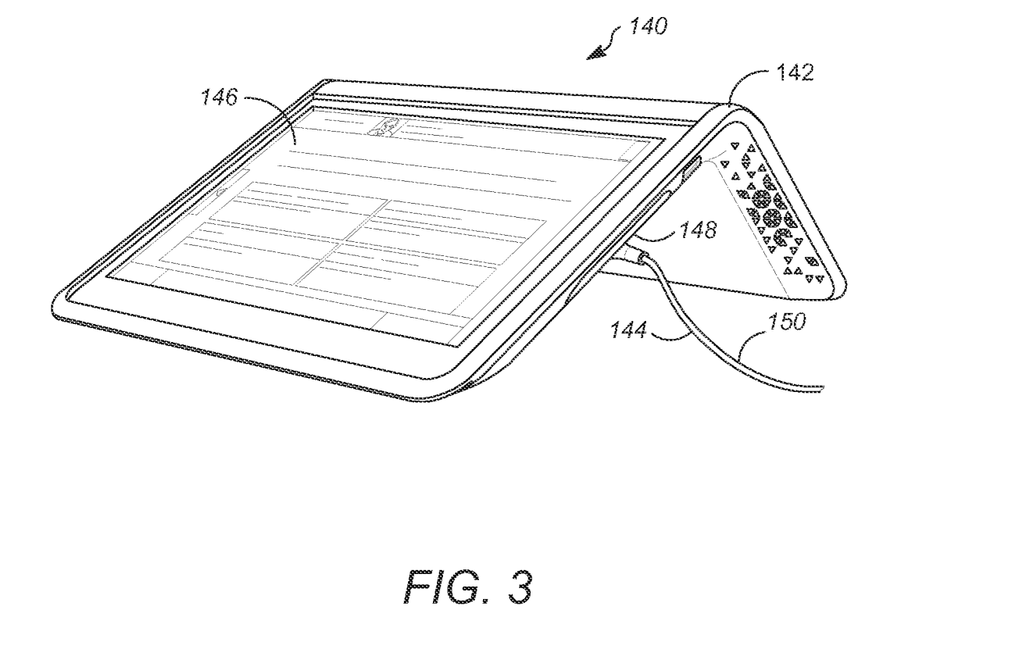
FIGS. 3 and 4 are perspective views of one embodiment of a programmer for use with the system of FIG. 1.

In one embodiment, the MRI clinic programmer 140 has a similar appearance and structure as the device clinic programmer 116. In another embodiment, depicted in FIG. 1, and also shown in FIGS. 3-5, the MRI clinic programmer 140 has a different appearance and structure compared to the device clinic programmer 116. In this embodiment, because the MRI professional 136 is likely to be an individual without significant training with IMD programming, the MRI clinic programmer 140 is provided with a simplified user interface and simplified functions compared to the device clinic programmer 116. It also possible for the simplified user interface depicted for the MRI clinic programmer 140 to be used as the device clinic programmer. Professionals with special training for IMDs can also benefit from a simplified user interface, especially when performing certain tasks.

Now referring to FIGS. 1 and 3-5, in one embodiment, the MRI clinic programmer 140 includes a housing 142 that is configured for portability by a user. For example, in one embodiment, the weight of the programmer 140 is less than three pounds. In another embodiment, the programmer 140 weighs less than two pounds. In one embodiment, a power source of the MRI clinic programmer 140 is contained within the housing 142. The programmer includes a touch screen 146 in one embodiment, which allows for both a graphical display and user input.

The programmer 140 includes a first communication module in the housing 142 configured to communicate with the prescription server 132 in order to retrieve the MRI prescription including the MRI settings that are associated with the IMD. A first communication link between the programmer 140 and the prescription server 132 may be via a pervasive wireless network, conventional phone lines, the Internet 130, or any other data connection. The programmer 140 can be used when it is not in communication with an IMD device, but is only in communication with the prescription server 132.

Generally, a pervasive wireless communication network is a communications network that can be used to directly communicate with a host computer without the need for a repeater device. A pervasive network includes those networks that are sufficiently prevalent or dispersed that an average person in the U.S. would be within range of interfacing with the network at some point during a normal daily routine. A pervasive wireless network typically has a relatively broad effective geographic span. There are many different usable pervasive wireless communication networks. One example is a wireless telephone network, such as a cellular telephone network. Other example embodiments of a pervasive wireless communication network include a wireless pager network, wireless wide area networks (WAN) such as those installed in certain public places like coffee shops, airports, schools, or municipalities, and wireless local area networks (LAN) including those following the standards set forth by the Institute for Electrical and Electronic Engineers (IEEE) in Standards 802.11(b) and (g).

The programmer 140 further includes a device communication module 144 for communicating with the IMD 110 over a device communication link. Now referring to FIG. 5, in one embodiment, the device communication module 144 includes a telemetry wand 146 on one end, an interface module 148 on the other end, and a flexible cord 150 connecting them. The telemetry wand 146 can be positioned over the IMD to enable inductive communication with the IMD. In an alternative embodiment, the device communication module uses radio frequency (RF) or other telemetry signals to communicate with the IMD.

Figure 4:
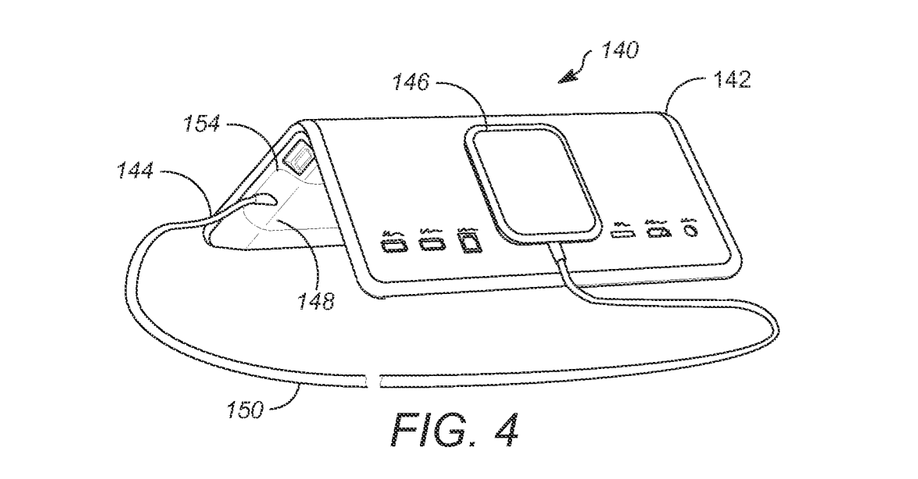
Figure 5:
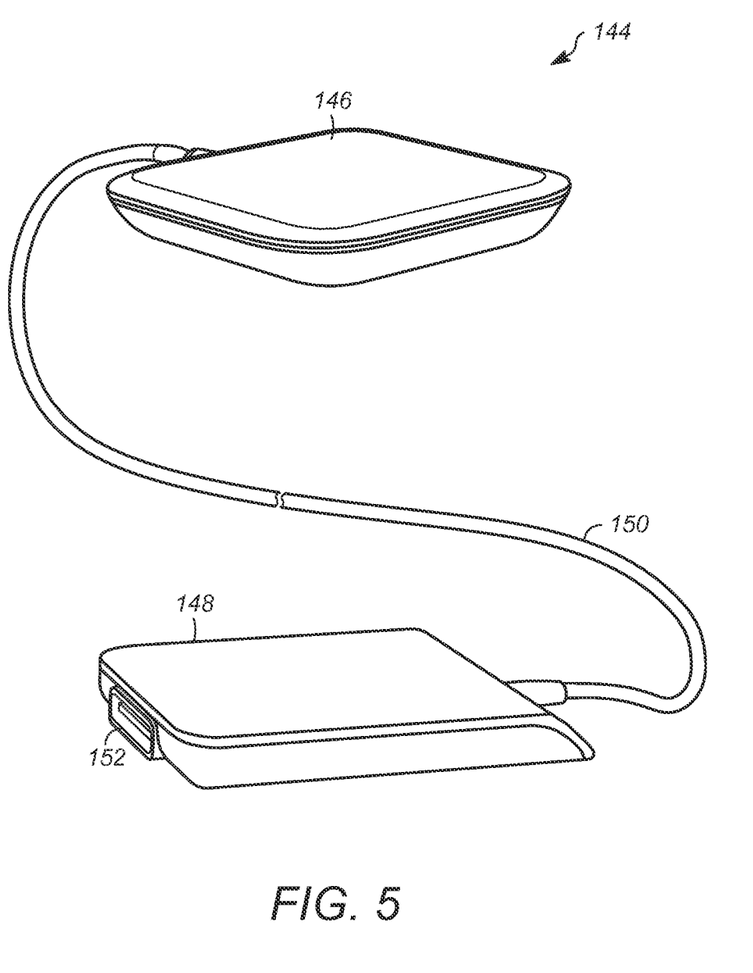
FIG. 5 is a perspective view of one example of a communication module of the programmer of FIGS. 3 and 4, for inductive communication with and IMD.

Now referring to FIGS. 4 and 5, in one embodiment, the interface module 148 is configured to be easily attached to and detached from the rest of the programmer 140. FIG. 5 shows the device communications module completely detached from the rest of the programmer 140. FIG. 4 illustrates the device communications module 144 attached to the rest of the programmer 140. Again referring to FIG. 5, the interface module 148 includes an interface connector structure 152 which reversibly connects to a mating connector structure (not shown) on the programmer 140. The connector structure is removable from and replaceable with the mating connector structure. The interface connector structure 152 is capable of carrying digital, bi-directional communication between the device communication module 144 and the rest of the programmer 140. The interface connector structure 152 is also capable of providing power to the device communication module 144 from the programmer 140. In one embodiment, a universal serial bus (USB) data transfer protocol is used. Other data transfer protocols and connector configurations could be used instead, such as an Ethernet connector, an IEE1394 interface (also known by the trade names of FireWire sold by Apple and Think sold by Sony) and a Thunderbolt interface. The interface connector structure 152 is a USB connector with additional power connections in one embodiment.

Now referring to FIG. 4, in order to connect the interface module 148 to the programmer, the interface module 148 slides into a recess 154 on the side of the programmer 140. When the interface module 148 is fully engaged in the recess 154, the connector 152 engages the mating connector of the programmer. In one embodiment, then the interface module 148 is fully engaged in the recess, the exterior of the interface module 148 is flush with an exterior surface of the programmer 140.

It is possible that the programmer 140 could be used with a device communication module 144 provided by a manufacturer different from the manufacturer of the programmer, but still be configured to attach to the programmer 140. Such an arrangement would allow the MRI professional 136 to use a single programmer 140 and user interface to make programming changes to IMDs from different manufacturers, thereby simplifying the equipment required at the MRI clinic 115.

In one embodiment shown in FIG. 4, the telemetry wand 146 is configured to mechanically fit into and be held by a cradle structure on a back side of the programmer 140, for the convenience of the user of the programmer.

Figure 6:
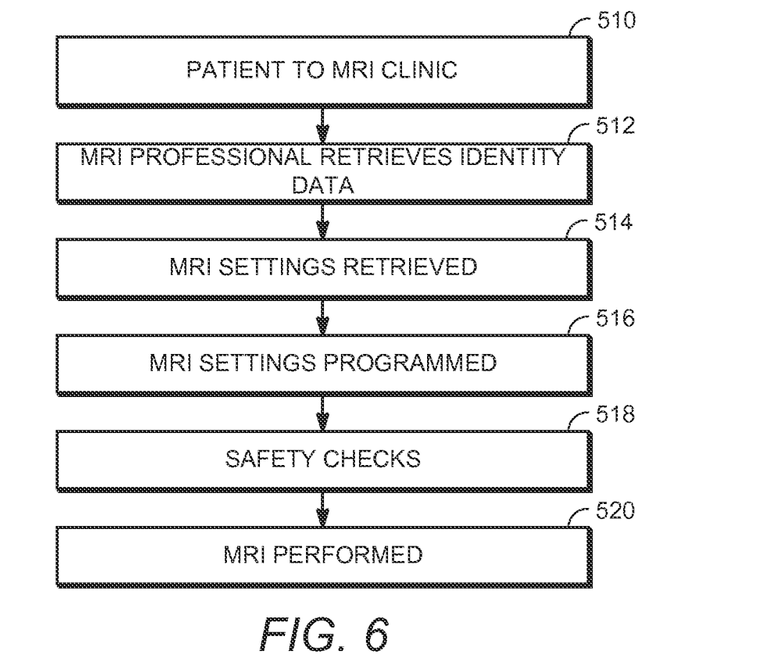
FIG. 6 is a flowchart showing a method for retrieving and programming MRI settings for a patient having an IMD.

FIG. 6 sets forth one embodiment of steps that can be taken at the MRI clinic to enable the patient to undergo an MRI procedure. The patient reports to the MRI clinic at step 510. The MRI professional 136 uses the MRI clinic programmer 140, selecting the MRI Mode on the screen of the programmer 140 in one embodiment. The programmer 140 communicates with the IMD 110 inductively, using the device communication module 144, and retrieves the identity data from the IMD 110 at step 512. In some embodiments, the telemetry module 146 is positioned over the IMD 110 during step 512 to facilitate inductive communication. The programmer 140 then communicates with the server 132 to retrieve an MRI prescription including MRI settings at step 514. The existence of an MRI prescription indicates that an MRI is permissible.

In some embodiments, the health care professional collects demographic data from the patient and enters that data into the programmer 140. Examples of demographic data that are collected in this embodiment include one or more of name, date of birth, social security number, health care system number, insurer number and other identifiers. The patient demographic data can be used to verify the patient identify.

In some embodiments, the retrieval of the identity data from the device automatically causes the programmer 140 to contact the server and to automatically retrieve any valid MRI prescription that is saved on the server. In some embodiments, both the collected patient demographic data and the IMD identity data are sent to the server in order to retrieve the MRI prescription.

In some embodiments, the programmer 140 performs range checking after the MRI prescription is retrieved and before the MRI settings are programmed. The range checking step compares the retrieved values for the numerical MRI settings values against expectations regarding these values. This step can help to identify if any problems during transmission of the MRI prescription have affected the MRI settings.

In some embodiments, additional steps such as encryption, digital signature, verification, confirmation and correctness checking are performed by the programmer 116, programmer 140, server 132 or a combination of these devices to ensure that the correct settings are programmed and that there is no problem with the transmission of the MRI prescription. Examples of how these steps can be performed are described in U.S. Patent Application No. 2007/0185547, which is hereby incorporated herein by reference in its entirety.

At step 516, the programmer 140 communicates with the IMD to program the MRI settings. At step 518, the programmer 140 provides the MRI professional 136 with a list of safety checks to be performed. Once those safety checks are complete, the MRI is performed at step 520.

Figure 7:
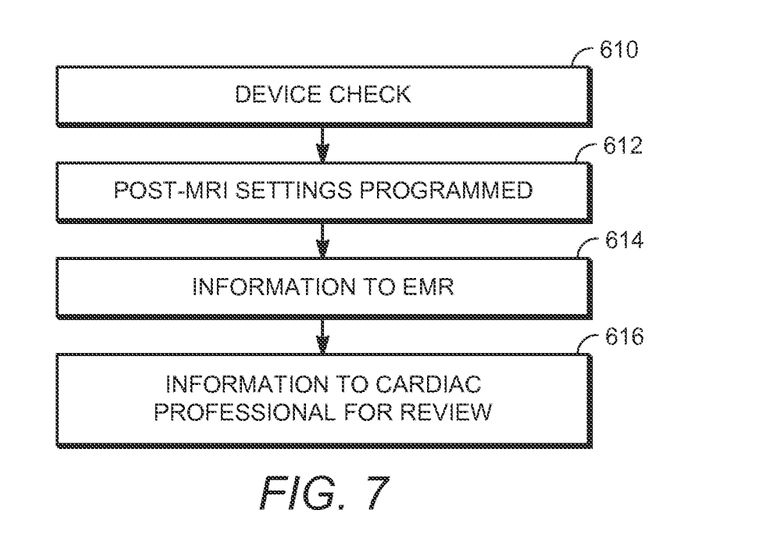
FIG. 7 is a flowchart showing a method for programming post-MRI settings to an IMD.

FIG. 7 sets forth one embodiment of steps that can be taken at the MRI clinic after the patient has undergone an MRI procedure. First, the programmer 140 is used to perform a device check on the IMD during step 610. In one embodiment, a device check involves two stages. In a first stage, the programmer is gathering data from the IMD and possibly running a series of tests on the IMD. In the second stage of the device check, the programmer is analyzing the data gathered and test results to determine if the IMD is operating as expected and to identify any concerns about the patient. If the device check results are normal or as expected, then the IMD can be programmed with post-MRI settings at step 612. The post-MRI settings may be identical to or different from pre-MRI settings. In some embodiments, a first set of post-MRI settings are implemented, and then after time passes or a further device check is carried out, a second set of post-MRI settings are implemented.

After the post-MRI settings are programmed, information from the device check and the settings restoration step is provided to the patient's electronic medical record at step 614. The information includes a summary of programming changes that were made to IMD settings in one embodiment and device check data. In addition, information from the post-MRI device check and the settings restoration is sent to one or more health care professionals for review at step 616. In one embodiment, a device check is also carried out after the post-MRI settings are programmed.

If concerns are identified during the device check performed after the MRI, or if the device check fails to complete, this information is displayed to the MRI professional via the programmer 140. In one embodiment, the post-MRI settings are not programmed in this situation.

Additional Device Programming Embodiments

The hardware and software described herein can also be applied outside of the MRI context. Instead of an MRI prescription, the system and method steps described herein can be used to execute a device prescription in order to change device parameters for a patient. These methods and systems are used where the health care professional with the expertise in making device programming changes is not in the same location as the patient at the time when the programming changes will to be implemented. The device prescription can be stored on an external storage location as described herein, and then retrieved from the storage location by a programming device at a later time. The device that retrieves the device prescription from the storage location can be referred to as a retrieval programmer. The alternatives and details described above for an MRI prescription and MRI clinic programmer also apply to a device prescription and a retrieval programmer used outside of the MRI context.

Device prescriptions can be useful in perioperative situations, as one example. Often, IMDs are turned off before surgery and then turned on after surgery. A device prescription to execute a device turn-off can be created and stored on a storage media. In one embodiment, the storage media is network connected to the apparatus that is used to create the device prescription. A device prescription form can be used to help the health care professional generate the device prescription. The use of a device prescription form can provide a simplified interface that is tailored for the perioperative situation. The apparatus used to create the device prescription can be a smart phone, a desktop computer, a laptop computer, a tablet computer or another device. Just before surgery, another health care professional can use a retrieval programmer to retrieve the device prescription from the storage media. In one embodiment, the storage media is network-connected and the retrieval programmer is also network connected. In one embodiment, the retrieval programmer allows the user to select a simplified user interface that is tailored to the perioperative situation, and simplifies the process of programming the device before surgery. The retrieval programmer can also provide, in some embodiments, checklists for pre- and post-surgery actions and device checks.

At the location where the device prescription will be implemented, one or more health care professionals are available to do one or more of assist the patient, retrieve identity data from the IMD, collect demographic data from the patient, check for a device prescription, program the device settings, conduct a medical procedure, program the IMD with post-procedure settings, and send a procedure report and device report to the patient's electronic medical record and other health care professionals.

A device prescription can be applied in many other contexts outside of the perioperative context. A device prescription provided a secure digital format for device-specialist health care professionals to deliver device-related physician orders to a uniquely identified patient.

One aspect of the device prescription systems and methods described herein is that the retrieval programmer is the device that initiates contact with a storage location, such as a server, to retrieve a device prescription with includes IMD programming instructions that have been stored there.

Further Options for Programmer Hardware

The programmers 116 and 140 can be for example, a programmer, a programmer/recorder/monitor device, a computer, a patient management system, a personal digital assistant (PDA), or the like. As used herein, the term programmer refers to a device that programs implanted devices and records data from implanted devices. A programmer may also allow monitoring of the implanted device. Exemplary programmer/recorder/monitor devices include the Model 3120 Programmer, available from Boston Scientific Corporation, Natick, Mass. The description of a programmer and its components can be applicable to a programmer 116 used in an device clinic or hospital, or a programmer 140 used in an MRI clinic, in various embodiments.

The programmer can include a user input device, such as a keyboard and/or a mouse. The programmer can include a video output channel and video output device, such as a video display for displaying video output. The displayed video output can include a user interface screen. In addition, the video display can also be equipped with a touch screen, allowing it to serve as a user input device as well.

The programmer, also sometimes referred to as an external interface device, can display real-time data and/or stored data graphically, such as in charts or graphs, and textually through the user interface screen. In addition, the programmer can present textual information to a user along with several response options. The programmer can also input and store a user's response to a question, and can store a user's text response in some embodiments.

In one embodiment, the external interface device or programmer, which can also be referred to as a user interface, is in communication with a prescription server 132. The programmer may be in communication with multiple servers having different purposes. The communication link between the programmer and the servers 132 and 133 may be via phone lines, the Internet 130, or any other data connection. The programmer can also be used when it is not in communication with an IMD device, but is only in communication with any of the servers.

In one embodiment, the programmer is capable of changing the operational parameters of the implantable medical device 110. Typically, programmers are used to interface with CRM devices in a clinic or hospital setting. In this context, the user of the programmer is a physician or trained technician.

Figure 8:
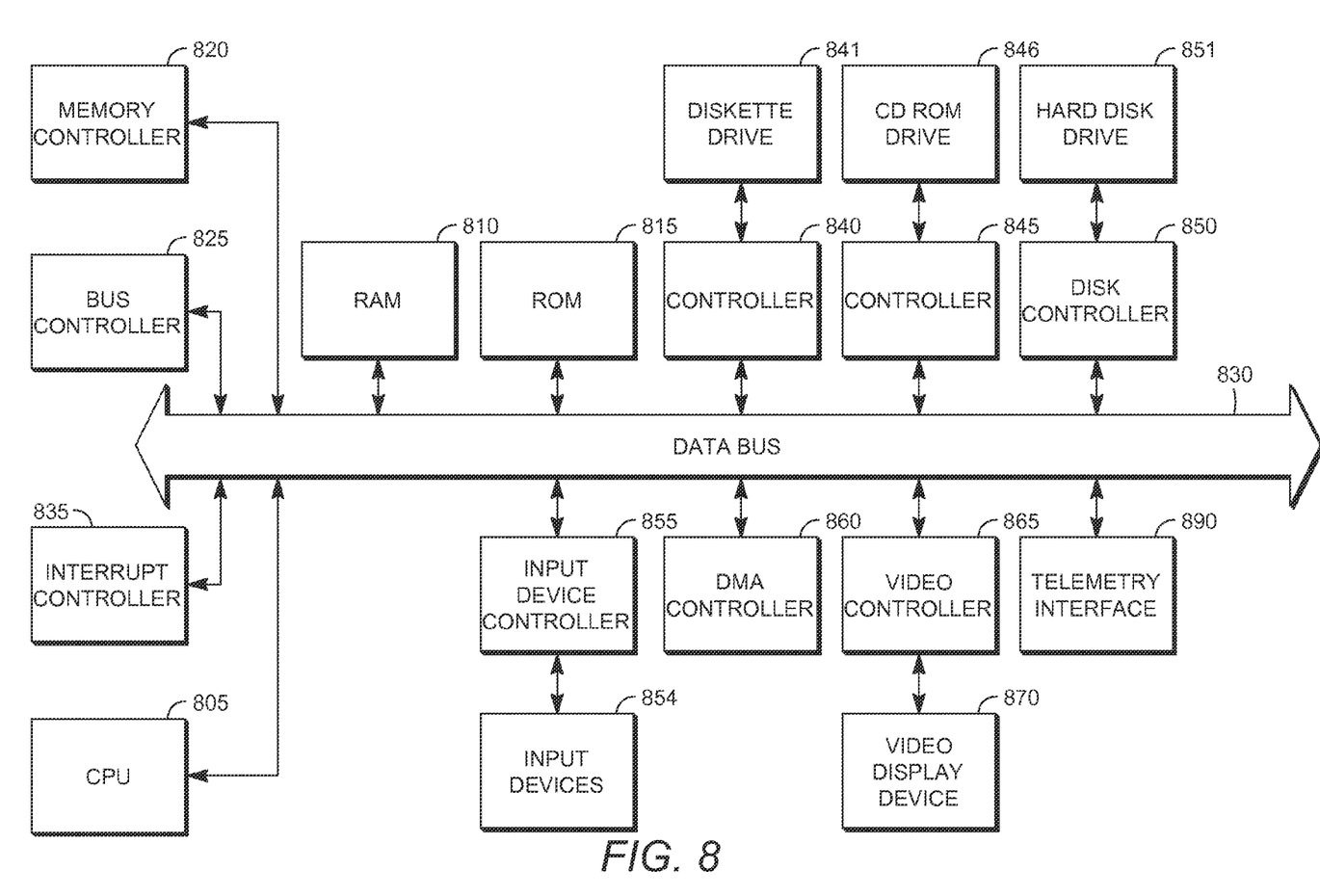
FIG. 8 is a schematic diagram of an implementation of the components of an external interface device such as a programmer, in accordance with various embodiments.

Programmers can include components common to many computing devices, such as user interface devices to display and receive information from users. Referring now to FIG. 8, a diagram of various components of one embodiment of a programmer is shown in accordance with some embodiments of the invention. However, it is not required that an external interface device or programmer have all of the components illustrated in FIG. 8.

In one embodiment, the programmer includes a central processing unit (CPU) 805 or processor, which may include a conventional microprocessor, random access memory (RAM) 810 for temporary storage of information, and read only memory (ROM) 815 for permanent storage of information. A memory controller 820 is provided for controlling system RAM 810. A bus controller 825 is provided for controlling data bus 830, and an interrupt controller 835 is used for receiving and processing various interrupt signals from the other system components.

Mass storage can be provided by diskette drive 841, which is connected to bus 830 by controller 840, CD-ROM drive 846, which is connected to bus 830 by controller 845, and hard disk drive 851, which is connected to bus 830 by controller 850. User input to the programmer system may be provided by a number of devices. For example, input devices 854 such as a keyboard and mouse can connect to bus 830 by input device controller 855. DMA controller 860 is provided for performing direct memory access to system RAM 810. A visual display is generated by a video controller 865 or video output, which controls video display 870. The external system can also include a telemetry interface 890 or telemetry circuit which allows the external system to interface and exchange data with an implantable medical device. It will be appreciated that some embodiments may lack various elements illustrated in FIG. 8.

A seeding module, parameter interaction module, pace timing optimization module and combinations thereof can be present in the programmer in different embodiments.

Hardware Options for IMDs

For convenience, the description herein will occasionally make reference to cardiac devices and issues with treating tachyarrhythmia. However, the methods and systems described herein are broadly applicable to many different types of IMDs, including non-cardiac devices. The applications discussed herein are intended to be exemplary and not limiting.

One embodiment of an IMD system will now be described in more detail with reference to FIG. 1, which is a schematic of an exemplary IMD system. The system can include an implantable medical device 110 disposed within a patient 112. The implantable medical device 110 can be in communication with a programmer 116 and 140. In some embodiments, communication between the implantable medical device 110 and the programmer can be via inductive communication through a wand 120 held on the outside of the patient 112 near the implantable medical device 110. However, in other embodiments, communication can be carried out via radiofrequency transmission, acoustically, or the like.

The implantable medical device 110 can include one or more implantable sensors in order to gather data regarding the patient 112. For example, the implantable medical device 110 can include an activity level sensor, a respiration sensor, a blood pressure sensor, an impedance sensor, or other sensors.

The implantable medical device 110 can be configured to store data over a period of time, and periodically communicate with the programmer 116 or programmer 140 or another device in order to transmit some or all of the stored data.

In one embodiment, the IMD 110 is a CRM device and is coupled by one or more leads 122 to the heart 126. Cardiac leads 122 include a proximal end that is coupled to IMD 110 and a distal end, coupled by an electrode or electrodes to one or more portions of a heart 126. The electrodes typically deliver cardioversion, defibrillation, pacing, or resynchronization therapy, or combinations thereof to at least one chamber of the heart 126. The electrodes may be electrically coupled to sense amplifiers to sense electrical cardiac signals.

Figure 9:
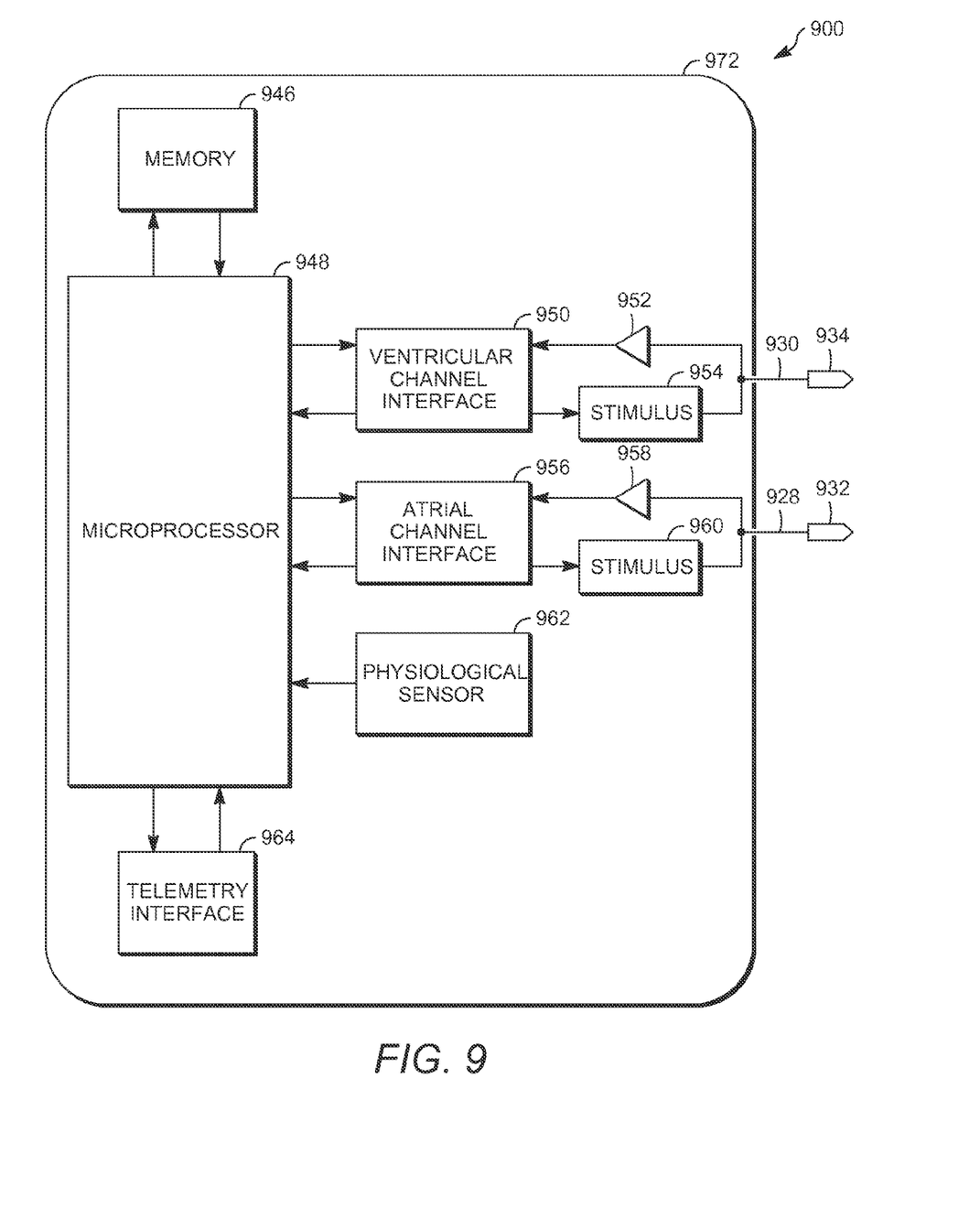
FIG. 9 is a block diagram of an implantable medical device.

Referring now to FIG. 9, some components of an exemplary implantable system 900 are schematically illustrated. The implantable medical system 900 can include an implantable medical device 972 coupled to one or more stimulation leads 930 and 928. The implantable device 972 can also include one or more physiological sensors 962, or other sensors, such as a pressure sensor, impedance sensor and others.

The implantable device can include a microprocessor 948 (or processor) that communicates with a memory 946 via a bidirectional data bus. The memory 946 typically comprises ROM or RAM for program storage and RAM for data storage. The implantable device can be configured to execute various operations such as processing of signals and execution of methods as described herein. A telemetry interface 964 is also provided for communicating with an external unit, such as a programmer device or a patient management system.

The implantable device can include ventricular sensing and pacing channels comprising sensing amplifier 952, output circuit 954, and a ventricular channel interface 950 which communicates bi-directionally with a port of microprocessor 948. The ventricular sensing and pacing channel can be in communication with stimulation lead 930 and electrode 934. The implantable device can include atrial sensing and pacing channels comprising sensing amplifier 958, output circuit 960, and an atrial channel interface 956 which communicates bi-directionally with a port of microprocessor 948. The atrial sensing and pacing channel can be in communication with stimulation lead 928 and electrode 932. For each channel, the same lead and electrode can be used for both sensing and pacing. The channel interfaces 950 and 956 can include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers.

A seeding module, parameter interaction module, pace timing optimization module and combinations thereof can be present in the device in different embodiments.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A system comprising:
    an implantable medical device (IMD) configured to be programmed with magnetic resonance imaging (MRI) settings for use during an MRI scan, wherein the IMD stores identity data that uniquely identifies the IMD or a patient having the IMD;
    an external storage media configured to receive MRI settings associated with the IMD from a device clinic programmer and configured to store the MRI settings associated with the IMD; and
    a retrieval programmer configured to perform the following steps:
        retrieve identity data from the IMD,
        initiate contact with the external storage media, retrieve the MRI settings associated with the IMD from the external storage media, wherein the MRI settings were received by the external storage media before the programmer retrieved the identity data from the IMD, and
        program the IMD using the MRI settings,
    wherein the MRI settings comprise a validity timeframe over which the MRI settings will be valid and after which the MRI settings cannot be retrieved from the external storage media.

2. The system of claim 1, wherein the retrieval programmer comprises:
    a first communication module configured to communicate with the external storage media to retrieve the MRI settings that are associated with the IMD; and
    a device communication module configured to communicate with the IMD to determine the identity of the IMD or patient and program the IMD with the MRI settings.

3. The system of claim 2 wherein the first communication module of the retrieval programmer is configured for communication with the external storage media over a pervasive wireless network.

4. The system of claim 2 wherein the first communication module of the retrieval programmer is configured for communication with the external storage media over a wired network.

5. The system of claim 2 wherein the device communication module of the retrieval programmer is configured for inductive communication with the IMD.

6. The system of claim 5 wherein the device communication module comprises a removable and replaceable connection to the retrieval programmer.

7. The system of claim 2 wherein the device communication module of the retrieval programmer is configured for radio frequency communication with the IMD.

8. The system of claim 1, the retrieval programmer further comprising a housing configured for portability by a user, wherein a power source is provided in the housing.

9. The system of claim 1 wherein the retrieval programmer is further configured to program the IMD with post-MRI settings.

10. The system of claim 9 wherein the retrieval programmer is further configured to perform a device check on the IMD.

11. The system of claim 1 wherein the external storage media is configured to store an MRI prescription, wherein the MRI prescription comprises MRI settings, the identity data and computer readable instructions to carry out the programming of the MRI settings on the IMD.

12. The system of claim 1 wherein the external storage media is a part of a server.

13. A system comprising:
an implantable medical device (IMD) configured to be programmed with magnetic resonance imaging (MRI) settings for use during an MRI scan and the IMD storing identity data that uniquely identifies the IMD or a patient having the IMD;
a server configured to receive an MRI prescription associated with the IMD from a device clinic programmer, and configured to store the MRI prescription associated with the IMD at a first time, wherein the MRI prescription comprises MRI settings, the identity data, and computer readable instructions to carry out the programming of the MRI settings on the IMD; and
a portable retrieval programmer comprising:
a housing configured for portability by a user;
a first communication module in the housing configured to communicate with the server to retrieve the MRI prescription associated with the IMD at a second time later than the first time, wherein the first communication module initiates contact with the server;
a device communication module connectible to and disconnectible from the housing and configured to inductively communicate with the IMD to retrieve the identity data and program the IMD with the MRI settings; and
a power source in the housing configured to supply power for components of the programmer,
wherein the MRI settings comprise a validity timeframe over which the MRI settings will be valid and after which the MRI settings cannot be retrieved from the server.

14. A method for conducting a magnetic resonance imaging (MRI) scan of a patient having an implantable medical device (IMD):
storing an MRI prescription for an IMD on an external storage media using a device clinic programmer at a first time, wherein the MRI prescription comprises MRI settings, identity data that uniquely identifies the IMD or the patient, and computer readable instructions to carry out the programming of the MRI settings on the IMD, wherein the IMD stores the identity data, wherein the MRI prescription is stored by a health care professional after review of safety concerns related to an MRI procedure;
identifying the IMD or patient using a retrieval programmer different from the device clinic programmer to communicate with the IMD; and
initiating contact with an external storage media to retrieve the device prescription using the retrieval programmer at a second time later than the first time
wherein the MRI settings comprise a validity timeframe over which the MRI settings will be valid and after which the MRI settings cannot be retrieved from the external storage media.

15. The method of claim 14 wherein the step of identifying comprises inductive communication between the retrieval programmer and the IMD.

16. The method of claim 14 further comprising the retrieval programmer performing safety checks before an MRI scan.

17. The method of claim 14 further comprising using the retrieval programmer after an MRI scan to program post-MRI settings of the IMD.

18. The method of claim 14 further comprising the retrieval programmer sending information to an electronic medical record, a health care professional, or both, wherein the information includes a summary of changes to IMD settings and device check data.

19. A system comprising:
an implantable medical device (IMD) configured to be programmed with IMD settings; and
a server configured to receive values for a device prescription comprising the IMD settings associated with the IMD or patient and configured to store the device prescription associated with the IMD or patient, wherein the device prescription further comprises the identity data and computer readable instructions to carry out the programming of the IMD settings on the IMD; and
a retrieval programmer, wherein the retrieval programmer comprises:
a first communication module configured to communicate with the server to retrieve the IMD settings that are associated with the IMD; and
a device communication module configured to communicate with the IMD and program the IMD with the IMD settings;
wherein the retrieval programmer is configured to initiate contact with the server to retrieve the IMD settings; wherein the IMD settings comprise a validity timeframe over which the IMD settings will be valid and after which the IMD settings cannot be retrieved from the server; and wherein the IMD settings were received by the external storage media before the retrieval programmer retrieved the identity data from the IMD.

* * * * *